(12) United States Patent
Flower (10) Patent No.: US 11,865,816 B2
(45) Date of Patent: Jan. 9, 2024

(54) PACKAGE SYSTEM

(71) Applicant: Kenneth F. Flower, Fremont, OH (US)

(72) Inventor: Kenneth F. Flower, Fremont, OH (US)

(*) Notice: Subject to any disclaimer, the term of this patent is extended or adjusted under 35 U.S.C. 154(b) by 165 days.

(21) Appl. No.: 17/333,552

(22) Filed: May 28, 2021

(65) Prior Publication Data

US 2021/0370652 A1 Dec. 2, 2021

Related U.S. Application Data

(60) Provisional application No. 63/032,002, filed on May 29, 2020.

(51) Int. Cl.
| | |
|---|---|
| *B32B 27/08* | (2006.01) |
| *A61L 9/04* | (2006.01) |
| *B32B 7/12* | (2006.01) |
| *B65B 11/00* | (2006.01) |
| *B65D 75/12* | (2006.01) |
| *B65D 75/58* | (2006.01) |
| *B32B 3/26* | (2006.01) |

(52) U.S. Cl.
CPC ............... *B32B 27/08* (2013.01); *A61L 9/04* (2013.01); *B32B 3/266* (2013.01); *B32B 7/12* (2013.01); *B65B 11/004* (2013.01); *B65D 75/12* (2013.01); *B65D 75/5855* (2013.01); *B32B 2439/40* (2013.01)

(58) Field of Classification Search
CPC ........... B32B 27/08; B32B 3/266; B32B 3/06; B32B 7/12; B32B 2439/40; B32B 3/14; B32B 3/26; B32B 2307/748; B32B 2307/758; A61L 9/04; B65B 11/004; B65D 75/12; B65D 75/5855
See application file for complete search history.

(56) References Cited

U.S. PATENT DOCUMENTS

| | | | |
|---|---|---|---|
| 7,926,735 B1* | 4/2011 | Mobley | A61L 9/04 239/57 |
| 8,114,451 B2 | 2/2012 | Sierra-Gomez et al. | |
| 2016/0022858 A1* | 1/2016 | D'Amico | A61L 9/048 422/123 |
| 2017/0021586 A1* | 1/2017 | Huffer | B32B 7/06 |
| 2018/0185536 A1* | 7/2018 | Santini | A61L 9/12 |

OTHER PUBLICATIONS

PackageRepublic, Oreo Cookie Package Usability Test, https://www.youtube.com/watch?v=JWnaSoq68c8, May 1, 2010 (Year: 2010).*
Oli, Outside the Box Thinking, https://o-I-i.blogspot.com/2010/02/thinking-outside-box.html, Feb. 16, 2010 (Year: 2010).*

* cited by examiner

*Primary Examiner* — Michael Zhang
(74) *Attorney, Agent, or Firm* — Jacob M. Ward; Ward Law Office LLC (57) ABSTRACT

A package system is provided that includes a main body having a bilayer thermoplastic laminated film structure including a first layer and a second layer with an adhesive layer disposed between the first layer and the second layer. The main body can further include an array of holes and a removable panel disposed on the array of holes. The removable panel can include a plurality of cutouts, where each one of the cutouts corresponds to one of the holes. The removable panel can be configured to be selectively pulled off the main body.

17 Claims, 5 Drawing Sheets

PACKAGE SYSTEM

CROSS-REFERENCE TO RELATED APPLICATIONS

This application claims the benefit of U.S. Provisional Application Ser. No. 63/032,002 filed on May 29, 2020. The entire disclosure of the above application is incorporated herein by reference.

FIELD

The present disclosure relates to plastic packaging and, more particularly, plastic packaging for a fragranced card such as a vehicle air freshener.

INTRODUCTION

This section provides background information related to the present disclosure which is not necessarily prior art.

Dispersed fragrances serve the purpose of presenting pleasurable aromas, freshening the air, concealing objectionable odors, and providing certain aromatherapy benefits. Once a fragrance compound has been designed and produced, it then must be packaged, delivered, stored, and ultimately be dispersed into an ambient environment.

One type of packaging is a sealed bottle of a liquid fragrance compound. However, this type of product delivery does not lend itself well to consumer level consumption. The problem is that a bottle of liquid does not include any convenient means for later dispersion of the fragrance at the end user level.

A more user-friendly approach is to permeate the fragrance compound into a physical structure that enables the vaporization and dispersion of the fragrance compound into the air. An example, the fragrance compound can be permeated into a card. Cards can be impregnated and then stored in a hermetically sealed container until they are deployed into service. Likely end users of such air freshener cards include individuals involved in the automotive services industries, such as a car wash employee, for example, who retrieves a card out of the hermetically sealed container and places it under the seat of an automobile. This action exposes the card to the air, where the fragrance compound can begin vaporization and dispersion.

The hermetically sealed container can include a plastic canister with an airtight lid that contains hundreds of fragrance cards. Such cards can be constructed of cardboard card and can include a brand name, manufacturer, and instructions for use printed thereon. Each card is damp with a specific quantity of fragrance compound when it is withdrawn from the container. The problem with this approach is that the card must ultimately rest on some surface, and that surface is then in physical contact with the damp fragrance compound, which can stain, discolor, and otherwise affect the surface. Similarly, the carwash employee must touch the card when it is retrieved, and thusly comes into contact with the fragrance compound. Of course, in the case of a car wash application, the hidden location of the resting surface obviates the problem of physical contact, and the car wash employee can be provided gloves to protect their fingers, or otherwise instructed in safe handling procedures for the cards.

There is also a consumer market for the aforementioned fragrance cards. This market differs substantially from the car wash market in that the consumer typically does not want to purchase a plastic canister of fragrance cards containing hundreds of cards. Rather, the consumer desires a much smaller number of cards, perhaps as few as just one card at a time. The cost of individual plastic canisters is prohibitive, so the cards are packaged into plastic or cellophane sleeves and sold individually, or in packages containing a small number of individually wrapped cards. The sleeve provides a hermetically sealed environment to contain the card and fragrance compound until the consumer tears open the sleeve to retrieve the card and place it into service. However, the aforementioned problems of human contact with the fragrance compound and contact with the surface on which the card ultimately rests are not addressed by the individually wrapped consumer product. These limitations greatly constrict the market range for such products.

Thusly, it can be appreciated that there is a need in the art for an apparatus and method of manufacture for a fragrance delivery product that disperses a fragrance compound while simultaneously addressing the problems in the art, and at a sufficiently low price point so as to be both desirable to consumers and profitable to manufacturers and retailers.

There is a continuing need for a package system that permits for the selective use of a fragranced material that is individually sealed in a package system while also militating against undesirable contact between the fragranced material and an exterior environment, in operation. Desirably, the package system also seals the fragranced material in a manner that militates against an evaporation of the fragrance or the degradation of adhesive on a removable panel over time.

SUMMARY

In concordance with the instant disclosure, a package system is provided that permits for the selective, metered use of a fragranced material that is individually sealed in a package system while also militating against the undesirable contact between the fragranced material and an exterior environment in operation, and which also seals the fragranced material in a manner that militates against an evaporation of the fragrance or the degradation of adhesive on a removable panel over time.

In certain embodiments, a package system is provided that includes a main body having a bilayer thermoplastic laminated film structure including a first layer and a second layer with an adhesive layer disposed between the first layer and the second layer. The main body can further include an array of holes and a removable panel disposed on the array of holes. The removable panel can include a plurality of cutouts, where each one of the cutouts corresponds to one of the holes. The removable panel can be configured to be selectively pulled off the main body. A fragranced material can be disposed in the main body.

In certain embodiments, a method of manufacturing a packaging system is provided that includes fabricating a bilayer thermoplastic laminated film structure. A sheet of the bilayer thermoplastic laminated film structure can be cut to form cut lines for an array of holes, cutouts, and a removable panel. The cut sheet of bilayer thermoplastic laminated film structure can be wrapped around a fragranced material. The free ends of the sheet of bilayer thermoplastic laminated film structure can be crimped. A first end and a second end of a main body formed from the bilayer thermoplastic laminated film structure can be crimped thereby sealing the main body around the fragranced material.

In an exemplary embodiment, the system may have a plastic package with a fragranced card, such as a vehicle air freshener. The plastic package may have a thin plastic main body that contains the fragranced card. The main body may have a first side and a second side, with the first side having an array of first holes and a second hole that is larger than the first holes. The array of first holes may be of any shape. The second hole may be configured to allow a cord attached to the fragranced card to be pulled through. The cord may be constructed out of cotton, plastic, elastic material, as non-limiting examples. One skilled in the art may select any suitable material to construct the cord within the scope of the present disclosure.

The plastic package of the system may also have a pull-and-peel panel that is coextensively formed and adhesively joined to the first side of the main body with a thin layer of releasable adhesive. Both the first holes and second hole and the peel-and-pull panel may be laser or die cut along tear lines so that they may be entirely separated from the first side of the main body by removing the peel-and-pull panel in operation. Prior to being removed, the peel-and-pull panel may cover all of the first holes and the second hole and seal the fragranced card. The sealing of the first holes and the second holes advantageously militates against an interaction of the fragrance with the adhesive, which otherwise might result in a degradation of the adhesive. Without being bound to any particular theory, it is believed that the laser or die cutting does not provide open slits or slots, and instead there is a tight interference fit between cut portions inside of the holes that creates the seal prior to the cut portions being removed by removal of the pull-and-peel panel as described further herein. Upon removal of the pull-and-peel panel, both the first holes and the second hole are open. The cord may then be pulled through the second hole and used to optionally hang the system, for example, on a rearview mirror of a vehicle. In other examples, the package system can be placed under a seat of the vehicle. The first holes permit the fragrance from the interior fragranced card to permeate into the surrounding environment, for instance, a vehicle interior.

It should be appreciated that the pull-and-peel panel and the releasable adhesive do not provide a visual indication of whether or not the panel has been previously removed by a margin gap between the panel and a coating. In particular, there is minimal or no coating of the releasable adhesive extending beyond the margins of the panel and thereby no tamper evident feature provided by the layer of the releasable adhesive between the panel and the first side of the main body. Instead, contrary to a margin method of tamper evidencing, the present technology may include at least one indicating arm permanently disposed on an edge of the peel-and-pull panel. The at least one indicating arm is selectively attached to the first side of the main body by laser or die cutting the shape of the at least one indicating arm into the first side of the main body while in a closed position. In operation, where the peel-and-pull panel has been pulled into an opened position, the at least one indicating arm will thereby also be pulled away from the first side of the main body. The pulling motion may result in the at least one indicating arm permanently detaching from the first side of the main body, providing a tamper evident feature due to the at least one indicating arm being visibly detached from the first side of the main body.

In an additional embodiment, the package system may further include a non-adhesive tab on the peel-and-pull panel. Advantageously, the non-adhesive tab may allow a user to more easily remove the peel-and-pull panel. One skilled in the art may select any suitable shape to form the non-adhesive tab within the scope of the present disclosure.

The package system may further include a plurality of peel-and-pull panels. In a particular example, the plurality of pull-and-peel panels may be in the form of strips. Each peel-and-pull panel may be oriented in a parallel position or a perpendicular position compared to a length of the fragrance card, as non-limiting examples. A skilled artisan may orient the plurality of peel-and-pull panels in any manner within the scope of the present disclosure. The plurality of pull-and-peel panels, as a whole, may be coextensively formed and adhesively joined to the first side of the main body with a thin layer of releasable adhesive. Each peel-and-pull panel may be laser or die cut along tear lines so that each peel-and-pull panel may be individually separated from the first side of the main body by selectively removing the peel-and-pull panel, in operation.

In should be appreciated that the peel-and-pull panel is not a decal placed on top of the plastic package. Instead, the plastic package of the present disclosure is a bilayer thermoplastic laminated film structure. The bilayer thermoplastic laminated film structure may have a first layer and a second layer adhered together with the releasable adhesive. Other methods of forming the bilayer thermoplastic film structure may involve heat, pressure, and other adhesives. A skilled artisan may select other methods for forming the bilayer thermoplastic film structure within the scope of the present disclosure.

The first layer may be laser cut or die cut to form the cut portion of the peel-and-pull panel. The second layer may be laser cut or die cut to form the cut portions of the first holes and the second hole. The plastic package may then be wrapped around the fragranced material and crimped on the second side of the plastic package.

In operation, as the peel-and-pull panel is lifted, the cut portions of the first layer and second layer will be removed from the first side of the main body. The removal of the cut portions of the first layer and second layer forms the first holes, the second hole, and the peel-and-pull panel. Advantageously, by die cutting or laser cutting the cut portions of the first layer and second layer, a controlled delamination process may be conducted when the peel-and-pull panel is lifted.

In certain embodiments, a method for assembling a package system is provided. The method may include a first step of providing a plastic package with a fragranced material, such as a vehicle air freshener. The plastic package may be further defined as a bilayer thermoplastic laminated film structure. The bilayer thermoplastic laminated film structure may have a first layer and a second layer adhered together with the releasable adhesive. The plastic package may further include a first side and a second side. The method may also include a second step of laser cutting or die cutting the first layer and second layer of the plastic package to form the cut portions of the first holes, the second hole, and the peel-and-pull panel. Then, the method may include a third step of wrapping the plastic package around the fragranced material. The method may then include a fourth step of crimping the second side of the package system. Next, the method may further have a fifth step of crimping a first end and a second end of the package system which seals the plastic package around the fragranced material.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

DETAILED DESCRIPTION

The following description of technology is merely exemplary in nature of the subject matter, manufacture and use of one or more inventions, and is not intended to limit the scope, application, or uses of any specific invention claimed in this application or in such other applications as can be filed claiming priority to this application, or patents issuing therefrom. Regarding methods disclosed, the order of the steps presented is exemplary in nature, and thus, the order of the steps can be different in various embodiments, including where certain steps can be simultaneously performed, unless expressly stated otherwise. "A" and "an" as used herein indicate "at least one" of the item is present; a plurality of such items can be present, when possible. Except where otherwise expressly indicated, all numerical quantities in this description are to be understood as modified by the word "about" and all geometric and spatial descriptors are to be understood as modified by the word "substantially" in describing the broadest scope of the technology. "About" when applied to numerical values indicates that the calculation or the measurement allows some slight imprecision in the value (with some approach to exactness in the value; approximately or reasonably close to the value; nearly). If, for some reason, the imprecision provided by "about" and/or "substantially" is not otherwise understood in the art with this ordinary meaning, then "about" and/or "substantially" as used herein indicates at least variations that can arise from ordinary methods of measuring or using such parameters.

Although the open-ended term "comprising," as a synonym of non-restrictive terms such as including, containing, or having, is used herein to describe and claim embodiments of the present technology, embodiments can alternatively be described using more limiting terms such as "consisting of" or "consisting essentially of" Thus, for any given embodiment reciting materials, components, or process steps, the present technology also specifically includes embodiments consisting of, or consisting essentially of, such materials, components, or process steps excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that can be recited in the art, even though element D is not explicitly described as being excluded herein.

When an element or layer is referred to as being "on," "engaged to," "connected to," or "coupled to" another element or layer, it can be directly on, engaged, connected, or coupled to the other element or layer, or intervening elements or layers can be present. In contrast, when an element is referred to as being "directly on," "directly engaged to," "directly connected to" or "directly coupled to" another element or layer, there can be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. can be used herein to describe various elements, components, regions, layers and/or sections, these elements, components, regions, layers and/or sections should not be limited by these terms. These terms can be only used to distinguish one element, component, region, layer, or section from another region, layer, or section. Terms such as "first," "second," and other numerical terms when used herein do not imply a sequence or order unless clearly indicated by the context. Thus, a first element, component, region, layer, or section discussed below can be termed a second element, component, region, layer, or section without departing from the teachings of the example embodiments.

Spatially relative terms, such as "inner," "outer," "beneath," "below," "lower," "above," "upper," and the like, can be used herein for ease of description to describe one element or feature's relationship to another element(s) or feature(s) as illustrated in the figures. Spatially relative terms can be intended to encompass different orientations of the device in use or operation in addition to the orientation depicted in the figures. For example, if the device in the figures is turned over, elements described as "below" or "beneath" other elements or features can then be oriented "above" the other elements or features. Thus, the example term "below" can encompass both an orientation of above and below. The device can be otherwise oriented (rotated 90 degrees or at other orientations) and the spatially relative descriptors used herein interpreted accordingly.

The present disclosure is drawn to articles of manufacture, systems, and ways of using and manufacturing a fragranced package or package system 100. Although described primarily herein with respect to fragranced cards for purpose of simplicity, it should be appreciated that other end uses including packaging of objects other than cards is contemplated and considered to be within the scope of the present disclosure. The embedding of chemicals or materials other than just fragrance is also contemplated. Non-limiting examples of further uses of the present disclosure can include packaging for sealing the aromas of foods such as coffee and related beverages, retaining the fragrance of scented air freshener stones, and sealing the pheromones of animal attractants such as animal lures and mouse traps.

The package system 100 can include a package having a main body 102 and a fragranced material 104 disposed within the main body 102 of the package. The fragranced material may be configured as a vehicle air freshener. As stated hereinabove, it should be appreciated that the fragranced card 104 can be replaced with other objects that are embedded with fragrance or other ingredients according to conventional means, as desired. Advantageously, the package system 100 of the present disclosure provides for the selective, metered use of a fragranced card 104 that is individually sealed in a package system 100 while also militating against the undesirable contact between the fragranced card 104 and an exterior environment in operation.

The main body 102 can be fabricated from a thermoplastic material, as a non-limiting example. In particular, the main body 102 can have a bilayer thermoplastic film structure. The bilayer thermoplastic film structure can include a first layer 106 and a second layer 108. An adhesive layer 110 can be disposed between the first layer 106 and the second layer 108. The adhesive layer 110 can include any suitable adhesive. Other methods of forming the bilayer thermoplastic film structure can involve heat, pressure, and other adhesives. A skilled artisan can select other methods for forming the bilayer thermoplastic film structure within the scope of the present disclosure.

The first layer 106 of the main body 102 can have an array of holes 112 formed therein. The holes 112 can be circular, as depicted in FIGS. 1-6. In non-limiting examples, each of the holes 112 can have a diameter of about $\frac{1}{8}^{th}$ of an inch to about $\frac{3}{8}^{th}$ of an inch. A skilled artisan can select other suitable shapes and dimensions for the holes 112, as desired.

The second layer 108 of the main body 102 can have a removable panel 114 formed therein. The removable panel 114 can be a pull-and-peel panel, as a non-limiting example. In certain embodiments, the removable panel 114 can be coextensive with a side of the main body 102. In other embodiments, the removable panel 114 can correspond to a length and a width of the array of holes 112. A skilled artisan can select suitable dimensions for the removable panel 114, as desired.

The removable panel 114 can have a plurality of cutouts 116 formed therein. The cutouts 116 can correspond to the array of holes 112, such that, each one of the cutouts 116 of the second layer 108 can seal one of the holes 112 of the first layer 106. In operation, the removable panel 114 can be pulled from the main body 102 by an operator. The cutouts 116 can be pulled away with the removable panel 114 and the array of holes 112 can be unsealed. The array of holes 112 can allow fragrance from the fragranced material to emanate out of the main body 102.

The array of holes 112 and the removable panel 114 can be laser or die cut along tear lines. In particular, the first layer 106 can be laser cut or die cut to form the array of holes 112. The second layer 108 can be laser cut or die cut to form the removable panel 114. Without being bound to any particular theory, it is believed that the laser or die cutting does not provide open slits or slots, and instead there is a tight interference fit between the holes 112 and the removable panel 114 that creates a seal prior to the removable panel 114 being removed. It should be appreciated that laser or die cutting along with the bilayer thermoplastic film structure including the array of holes 112 and cutouts 116 can militate against an undesirable interaction with the adhesive layer 110. In particular, the adhesive layer 110 is entirely disposed between the first layer 106 and the second layer. The cutouts 116 can seal each of the holes 112, which seals the first layer 106, thereby, separating the fragranced card 104 from the adhesive layer 110.

The main body 102 can further include a pull tab 118. The pull tab 118 can be formed in an end of the removable panel 114. The pull tab 118 can be substantially free of adhesive. The pull tab 118 can allow the user to more easily pull the removable panel 114 away from the main body 102, in operation. A skilled artisan can select any suitable shape and dimension for the pull tab 118, as desired.

Figure 6:
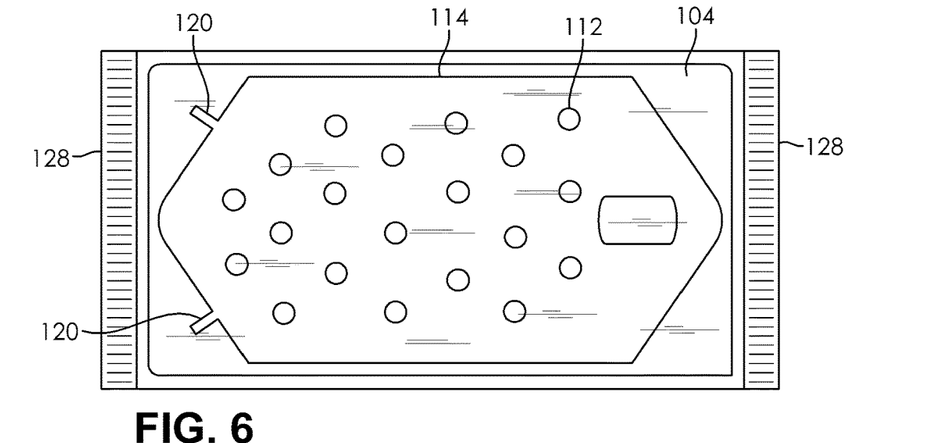
FIG. 6. is a top plan view of the package system according to yet another embodiment of the present disclosure, depicting a pull tab on the removable panel, and further showing indicating arms where each is in a closed position.
Figure 7:
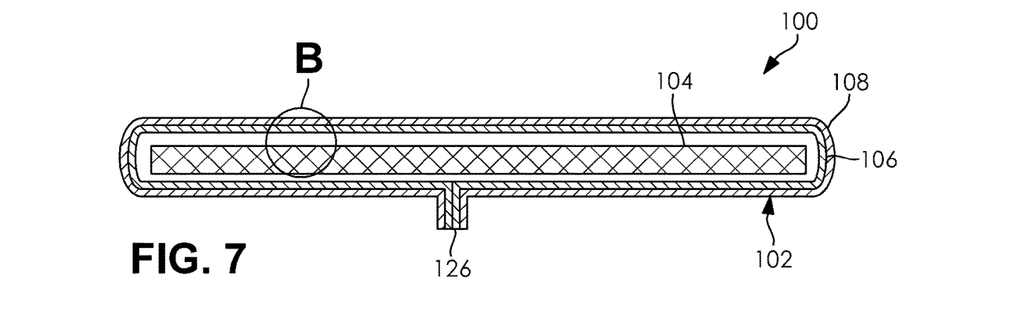
FIG. 7 is a cross-sectional front elevational view taken at section line A-A in FIG. 1, depicting the plastic package wrapping around the card and crimped on the second side of the plastic package system, according to one embodiment of the present disclosure.
Figure 8:
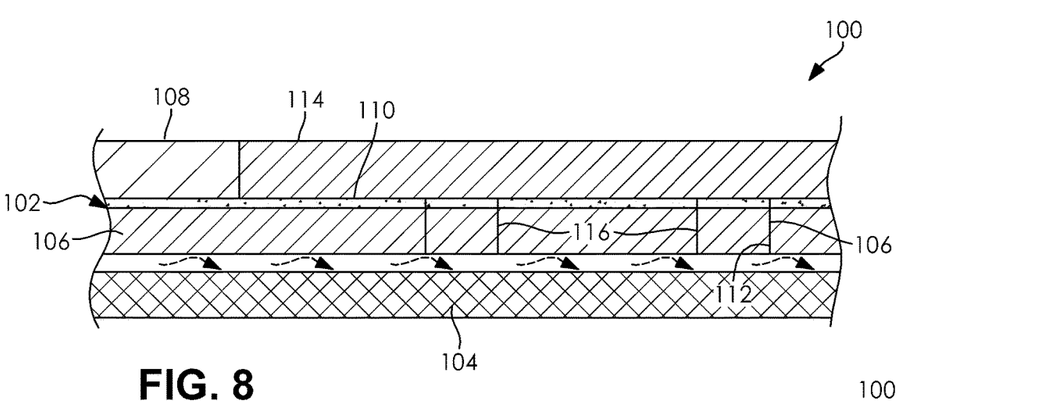
FIG. 8 is a cross sectional front elevational view taken at callout B in FIG. 7, depicting the depicting the bilayer thermoplastic laminated film structure of the package system with arrows depicting the flow of fragrance from the fragranced card within the main body.
Figure 9:
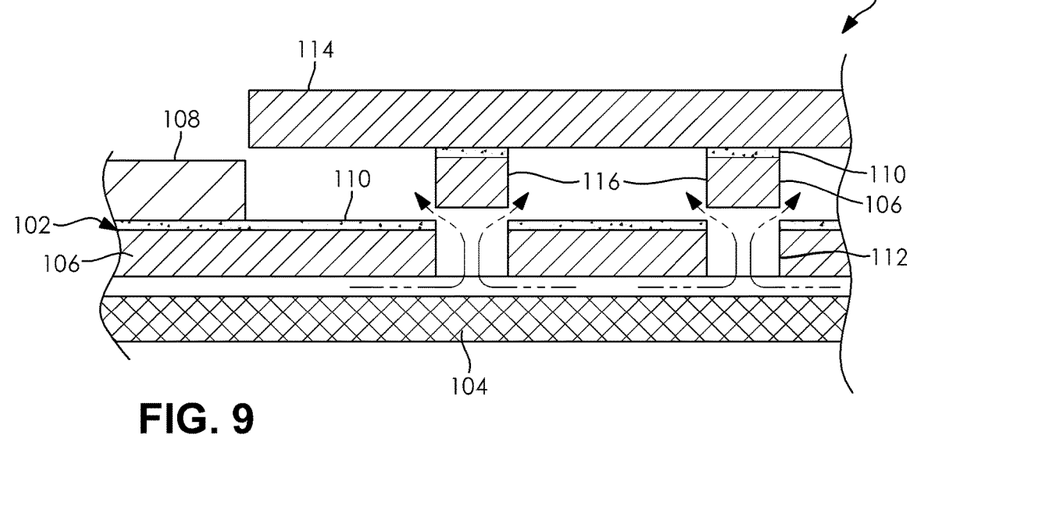
FIG. 9 is a cross sectional front elevational view taken at callout B in FIG. 7, depicting the removable panel being pulled from the main body of the plastic package with arrows depicting a flow of fragrance from the fragranced card outside the main body.
Figure 10:
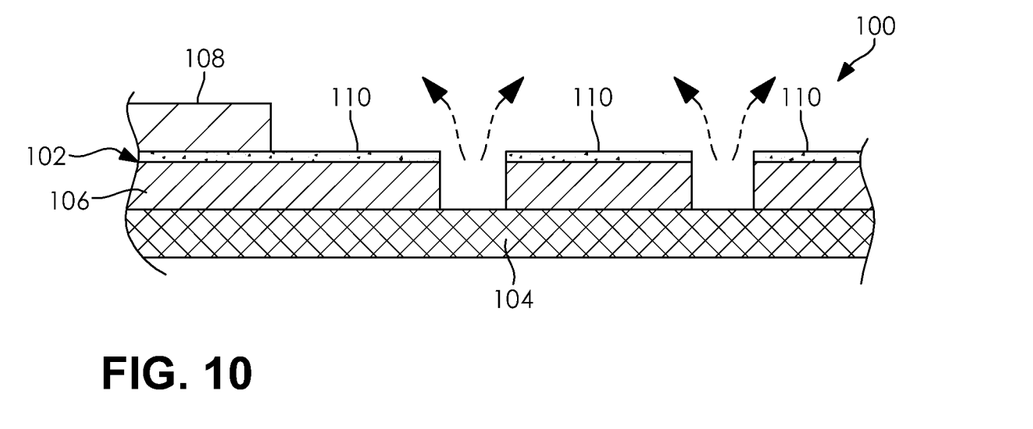
FIG. 10 is a cross sectional front elevational view taken at callout B in FIG. 7, depicting the removable panel fully removed from the main body of the plastic package with arrows depicting a flow of fragrance from the fragranced card outside the main body.

The main body 102 can include at least one indicating arm 120, for example, as shown in FIG. 6. The indicating arm 120 can be permanently disposed on an edge of the removable panel 114, for example, adjacent to the pull tab 118. In operation, where the removable panel 114 has been pulled into an opened position, the indicating arm 120 will thereby also be pulled away from the main body 102. The pulling motion can result in the indicating arm 120 permanently detaching from the main body 102, providing a tamper evident feature due to the indicating arm 120 being visibly detached from the main body 102.

Figure 1:
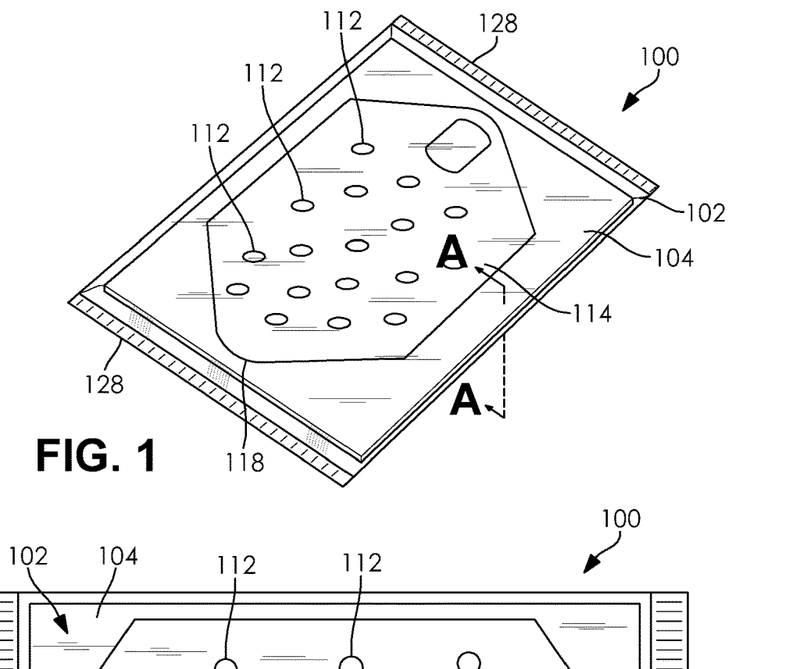
FIG. 1 is a top perspective view of a package system according to one embodiment of the present disclosure.
Figure 2:
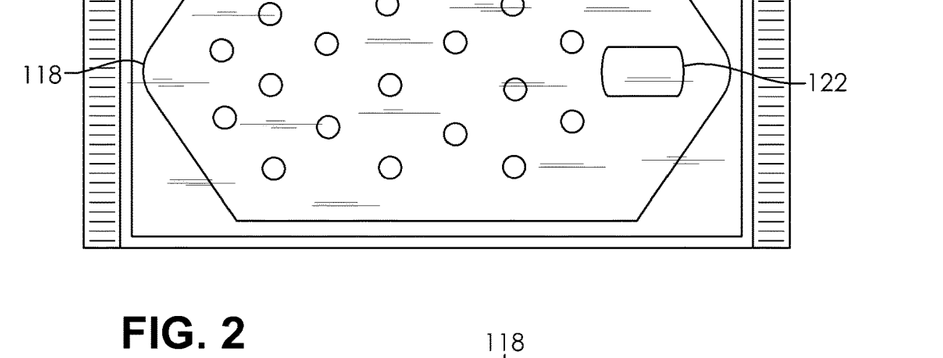
FIG. 2 is a top plan view of the package system shown in FIG. 1.
Figure 3:
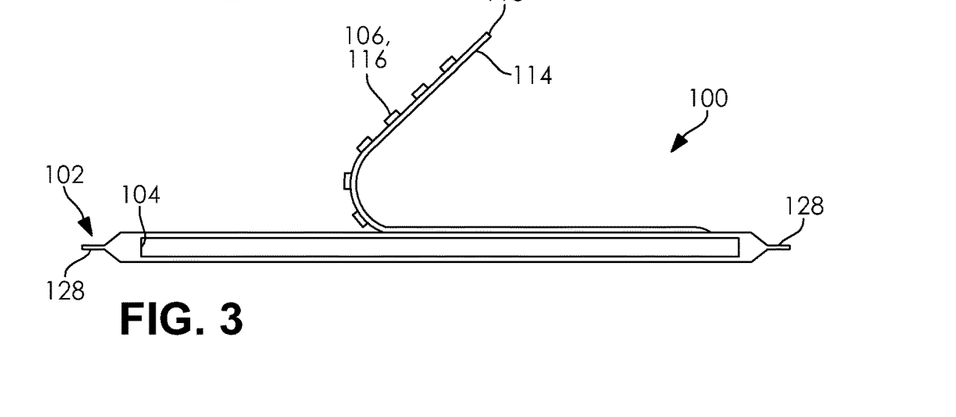
FIG. 3 is a side elevational view of the package system of FIG. 1 depicting the removable panel being removed from a main body of a plastic package, according to one embodiment of the present disclosure.
Figure 4:
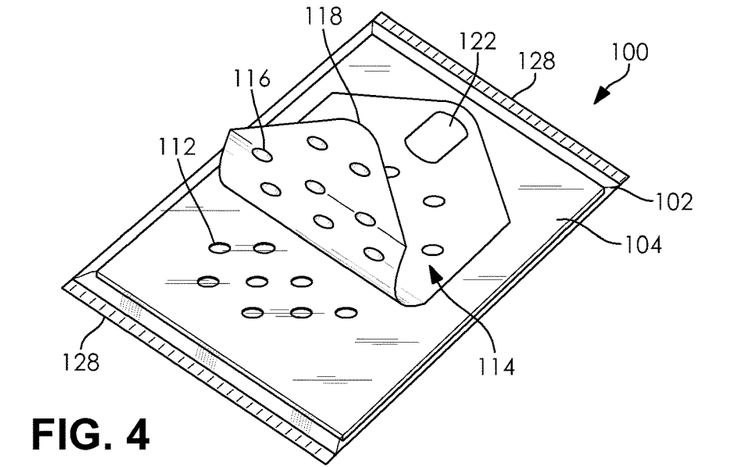
FIG. 4 is a top perspective view of the package system shown in FIG. 1, depicting the removable panel being removed from a main body of a plastic package, according to one embodiment of the present disclosure.
Figure 5:
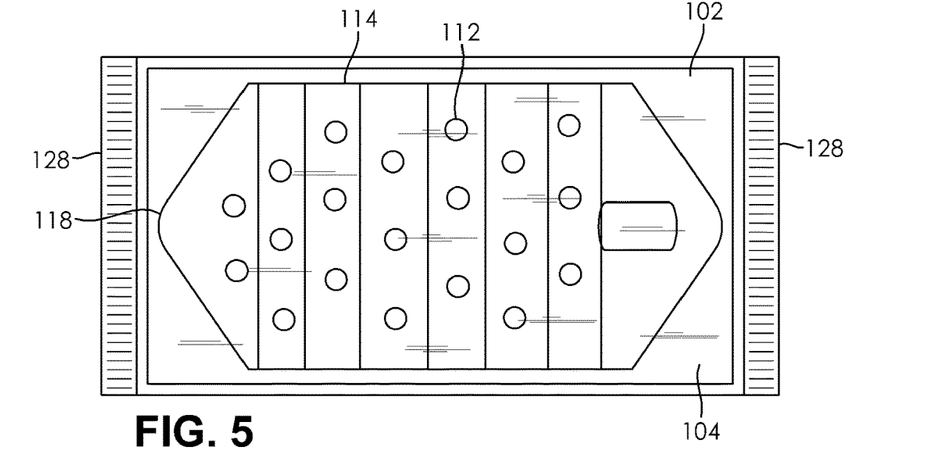
FIG. 5 is a top plan view of the package system according to another embodiment of the disclosure, depicting a plurality of removable panels on the package system, according to another embodiment of the present disclosure.

In one embodiment, as shown in FIG. 5, the package system 100 can further include a plurality of removable panels 114. In a particular example, the plurality of removable panels 114 can be in the form of strips. The plurality of removable 1 panels 114 can be oriented in a parallel position or a perpendicular position compared to a length of the fragrance card 104, as non-limiting examples. A skilled artisan can orient the plurality of removable panels 114 in any manner within the scope of the present disclosure.

The plurality of removable panels 114, as a whole, can be coextensively formed and adhesively joined of the main body 102. The plurality of removable panels 114 can be formed by laser or die cut along tear lines on the removable panel 114 to form the multiple removable panels 114. Each one of the plurality of removable panels 114 can be individually and selectively separated from the main body 102 by removing each of the plurality of removable panels 114, in operation. Advantageously, the multiple panels 114 can allow the user to determine a quantity of holes 112 to unseal, which can limit the amount of fragrance that can emanate from the main body 102, and thus, allow the user to control a volume of scent.

Figure 11:
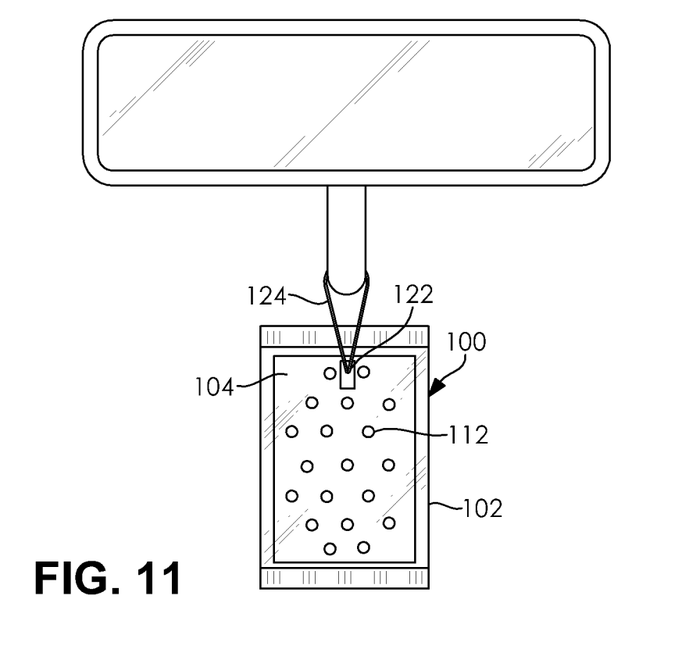
FIG. 11 is a front elevational view of the package system, depicted in use hanging from a rearview window of a vehicle, according to a further embodiment of the present disclosure.

In certain embodiments, the main body can have an aperture 122 as shown in FIG. 11. The aperture 122 can be comparatively larger than each of the holes 112. The aperture 122 can be configured to allow a cord 124 attached to the fragranced card 104 to be pulled through. The cord 124 can be constructed out of cotton, plastic, elastic material, as non-limiting examples. One skilled in the art can select any suitable material to construct the cord 124 within the scope of the present disclosure.

Figure 12:
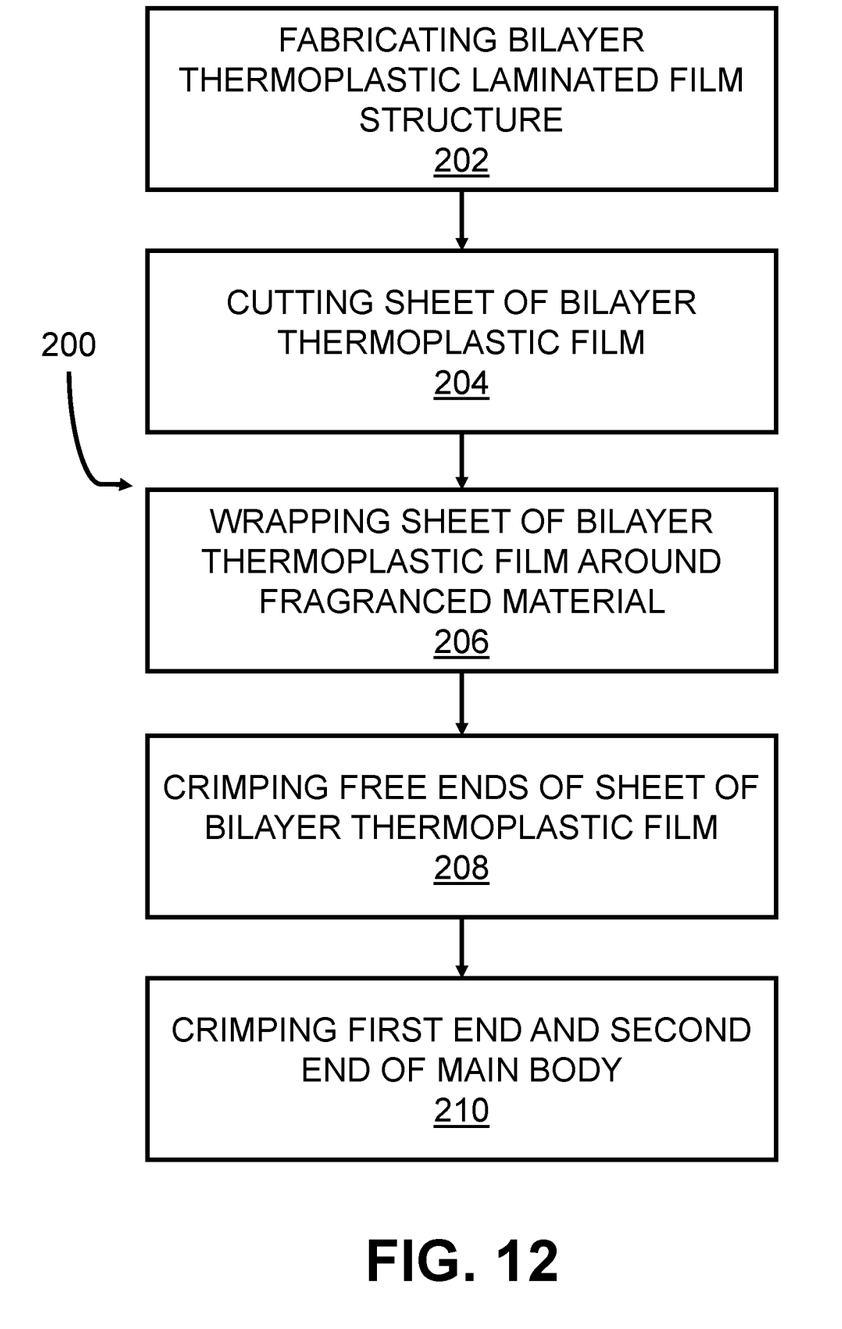
FIG. 12 is a flow chart depicting a method of manufacturing the packaging system of FIG. 1, according to a further embodiment of the present disclosure.

In a further embodiment, for example as shown in FIG. 12, the present disclosure relates to a method 200 for assembling the package system 100. The method 200 can include a first step 202 of fabricating the bilayer thermoplastic laminated film structure. This can include providing the first layer 106 and the second later 108 and disposing the adhesive layer together. The layers 106, 108 can be laminated together with the adhesive layer 110 to form a sheet of the bilayer thermoplastic laminated film. The lamination process can include an application of pressure or heat, as desired by a skilled artisan.

The method 200 can include a second step 204 of cutting the sheet of the bilayer thermoplastic film. In particular, this step can include cutting the cut lines for the array of holes 112 and the cutouts 116 from the first layer 106 and cutting the cut lines for the removable panel 114 from the second layer 108. As described hereinabove, the cutting can include a laser cutting or a die cutting process. These types of cutting are believed to maintain a tight interference fit within the cutlines between the holes 112 and the cutouts 116, such that, the adhesive layer 110 stays sealed between the first layer 106 and the second layer 108 until the removable panel 114 is pulled away from the main body 102. Advantageously, this can militate against an undesirable interaction between the fragranced material 104 and the adhesive layer 110.

Then, the method 200 can include a third step 206 of wrapping the sheet of the bilayer thermoplastic film around the fragranced material 104. In particular, the sheet of sheet of the bilayer thermoplastic film can be wrapped where an entirety of the removable panel is disposed adjacent to a side of the fragranced material 104. Free ends of the sheet of the bilayer thermoplastic film can be disposed on an opposite side of the fragranced material 104.

The method 200 can then include a fourth step 208 of crimping the free ends to form a crimped edge 126 of sheet of the bilayer thermoplastic film. Next, the method 200 can further have a fifth step 210 of crimping a first end and a second end of the main body 102 to form crimped ends 128, which seals the main body 102 around the fragranced material 104.

In operation, the user can provide the package system 100 where the fragranced material 104 is sealed within the main body 102. Prior to being removed, the removable panel 114 covers all of the array of holes 112 and aperture 122. Upon removal of the removable panel 114, the cutouts 116 are retained on the removable panel 114 by the adhesive layer and the array of holes 112 are opened. The cord 124 can then be pulled through the aperture 122 and used to optionally hang the system 100, for example, on a rearview mirror of a vehicle, as shown in FIG. 11. In other examples, the package system can be placed under a seat of the vehicle. The array of holes 112 permit the fragrance from the interior fragranced card 104 to permeate into the surrounding environment, for instance, a vehicle interior.

Advantageously, the package system 100 of the present disclosure provides for the selective, metered use of a fragranced card 104 that is individually sealed in a package system 100 while also militating against the undesirable contact between the fragranced card 104 and an exterior environment in operation, and which also seals the fragranced card 104 in a manner that militates against an evaporation of the fragrance or the degradation of adhesive on a removable panel over time.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments can be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, compositions, and methods can be made within the scope of the present technology, with substantially similar results.

What is claimed is:

1. A package system, comprising:
a main body defining a container with a top side, a bottom side, a first side, a second side, a first end, and a second end, the main body having a bilayer thermoplastic laminated film structure including a first layer and a second layer with an adhesive layer disposed between the first layer and the second layer, wherein the first layer, the second layer, and the adhesive layer are formed as a continuous sheet,
the main body further including an array of holes, an aperture, and a removable panel disposed on the array of holes and the aperture, the removable panel including a plurality of cutouts, each one of the cutouts corresponding to one of the holes, the removable panel configured to be selectively pulled off the main body, the removable panel formed in the second layer and having a first removable panel end and a second removable panel end, with each of the first removable panel end and the second removable panel end being coextensive with the top side of the main body, the first removable panel end spaced apart from the first end of the main body, and the second removable panel end spaced apart from the second end of the main body, the aperture being comparatively larger than each one of the holes of the array of holes, and the aperture formed through only the top side of the main body and adjacent the first end of the main body; and
a fragranced material disposed in the main body, the fragranced material having a cord configured to be deployed through the aperture of the main body upon the removable panel being pulled off the main body,
wherein the bilayer thermoplastic laminated film structure is wrapped around an entirety of the fragranced material with a crimped edge and crimped ends, the crimped edge disposed along a central axis of the main body, and one of the crimped ends disposed at each of the first end of the main body and the second end of the main body, and the first side of the main body and the second side of the main body are continuous, uninterrupted, and not crimped.

2. The package system of claim 1, wherein the fragranced material includes a vehicle air freshener.

3. The package system of claim 1, wherein the adhesive layer of the bilayer thermoplastic laminated film structure is entirely contained between the first layer and the second layer of the bilayer thermoplastic laminated film structure.

4. The package system of claim 1, wherein the main body includes cutlines that define the removable panel, the cutouts, the aperture, and the array of holes.

5. The package system of claim 4, wherein the cutlines are formed from a die cutting process or a laser cutting process.

6. The package system of claim 1, wherein the removable panel is fabricated from the second layer of the bilayer thermoplastic laminated structure.

7. The package system of claim 1, wherein the cutouts are fabricated from the first layer of the bilayer thermoplastic laminated structure.

8. The package system of claim 1, wherein the array of holes is formed in the first layer of the bilayer thermoplastic laminated structure.

9. The package system of claim 1, wherein the cutouts are secured to the removable panel via the adhesive layer of the bilayer thermoplastic structure.

10. The package system of claim 1, wherein the removable panel is fabricated from the second layer of the bilayer thermoplastic laminated structure, the cutouts are fabricated from the first layer of the bilayer thermoplastic laminated structure, and the array of holes is formed in the first layer of the bilayer thermoplastic laminated structure.

11. The package system of claim 10, wherein the cutouts are secured to the removable panel via the adhesive layer of the bilayer thermoplastic structure.

12. The package system of claim 1, wherein an entirety of the array of holes is disposed in the top side of the main body.

13. The package system of claim 1, wherein the removable panel is comprised by a plurality of removable panels.

14. The package system of claim 1, wherein the removable panel includes an indicating arm configured to indicate if the removable panel has been pulled from the main body.

15. The package system of claim 1, wherein the cutouts form a tight interference fit with the array of holes when the removable panel is disposed on the main body, and the cutouts are pulled away with the removable panel when pulled from the main body.

16. The package system of claim 1, wherein the removable panel includes a pull tab defined by the second removable panel end and disposed adjacent the second end of the main body that is substantially free of adhesive.

17. A method of manufacturing a packaging system, the method comprising steps of:
fabricating a bilayer thermoplastic laminated film structure including a first layer and a second layer with an adhesive layer disposed between the first layer and the second layer, wherein the first layer, the second layer, and the adhesive layer are formed as a continuous sheet;
cutting the continuous sheet of the bilayer thermoplastic film structure to form cut lines for an array of holes, cutouts, an aperture, and a removable panel;
wrapping the sheet of the bilayer thermoplastic film structure around an entirety of a fragranced material to formed a main body defining a container with a top side, a bottom side, a first side, a second side, a first end, and a second end;
forming a crimped edge disposed along a central axis of the main body by crimping free edges of the continuous sheet of the bilayer thermoplastic laminated film structure;
forming crimped ends disposed at each of the first end of the main body and the second end of the main body by crimping free ends of the continuous sheet of the bilayer thermoplastic film structure, thereby sealing the main body around the entirety of the fragranced material,
wherein each one of the cutouts corresponds to one of the holes, and the removable panel is configured to be selectively pulled off the main body, the removable panel formed in the second layer and having a first removable panel end and a second removable panel end, with each of the first removable panel end and the second removable panel end being coextensive with the top side of the main body, the first removable panel end spaced apart from the first end of the main body, and the second removable panel end spaced apart from the second end of the main body, the aperture being comparatively larger than each one of the holes of the array of holes, and the aperture formed through only the top side of the main body and adjacent the first end of the main body, the fragranced material having a cord configured to be deployed through the aperture of the main body upon the removable panel being pulled off the main body.

* * * * *